US00PP31785P2

(12) United States Plant Patent
Hansen

(10) Patent No.: US PP31,785 P2
(45) Date of Patent: May 19, 2020

(54) ***HEUCHERA* PLANT NAMED 'SMOKE AND MIRRORS'**

(50) Latin Name: ***Heuchera* hybrid**
Varietal Denomination: Smoke and Mirrors

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/602,321

(22) Filed: Sep. 13, 2019

(51) Int. Cl.
*A01H 5/02* (2018.01)
*A01H 6/80* (2018.01)

(52) U.S. Cl.
USPC ..... Plt./440
CPC ..... *A01H 6/80* (2018.05)

(58) Field of Classification Search
USPC ..... Plt./440
CPC ..... A01H 5/02
See application file for complete search history.

*Primary Examiner* — Kent L Bell

(57) ABSTRACT

The new and distinct hybrid of *Heuchera* plant named 'Smoke and Mirrors' with rounded, slightly shiny, shallowly-dissected leaf blades having silvery coloration with strong purplish undertones in spring and becoming silver with deep green surrounding the veins. The new plant has deep reddish calyces on mostly-upright highly-branched panicles. The new plant is vigorous, resists melting out in high heat and humidity and produces medium clumps with many dense leaves and is useful in the landscape or in containers.

1 Drawing Sheet

Botanical denomination: *Heuchera* hybrid.
Variety denomination: 'Smoke and Mirrors'.

STATEMENT REGARDING PRIOR DISCLOSURES UNDER 37 CFR 1.77(B)(6)

The first sales of *Heuchera* 'Smoke and Mirrors' was by Walters Gardens, Inc. on Oct. 2, 2018 to Plant Delights Nursery, Inc. Walters Gardens, Inc. obtained the new plant and information about the new plant directly from the inventor. No plants of *Heuchera* 'Smoke and Mirrors' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to a new and distinct cultivar of Coral Bells in the Saxifragaceae family and given the cultivar name of 'Smoke and Mirrors'. *Heuchera* 'Smoke and Mirrors' was hybridized by the inventor on Apr. 18, 2013 at a wholesale perennial nursery in Zeeland, Mich., USA and assigned the breeder code 13-610-1. The seed or female parent was the proprietary, unreleased and unnamed hybrid assigned the breeder code 12-242-08 (not patented) and the male parent was the proprietary unreleased and unnamed hybrid assigned the breeder code K11-52-15 (not patented).

*Heuchera* 'Smoke and Mirrors' was first selected in the fall of 2015 and passed final evaluation in the fall of 2017 from among thousands of other seedlings from the same cross and hundreds of other crosses. *Heuchera* 'Smoke and Mirrors' has been asexually propagated by division at the same nursery in Zeeland, Mich. in 2015 and by careful shoot tip tissue culture propagation, and the resultant plants have remained stable and continued to exhibit the same characteristics as the original plant for multiple generations.

BRIEF SUMMARY OF THE INVENTION

The following traits distinguish *Heuchera* 'Smoke and Mirrors' as a distinct hybrid plant. In comparison to the female parent and the cultivars hybridized to produce the female parent, *Heuchera* 'Smoke and Mirrors' has more flatter, more silver leaves with less purple undertones in mid-season, with deep red calyces on upright, medium-density, compound-branched stems. The most similar cultivars known to the inventor are 'Silver Gumdrop' U.S. Plant Pat. No. 29,207 and 'Stainless Steel' U.S. Plant Pat. No. 23,349. 'Silver Gumdrop' maintains more rose-colored blushing in the silver foliage and the overall habit is smaller with shorter flower scapes producing darker flowers, and smaller leaf blades than the new plant. 'Stainless Steel' has white flowers and the foliage has a more brown undertone. 'Mocha' U.S. Plant Pat. No. 18,386 has foliage that is more brownish-purple and the flowers are creamy-white colored. 'Milan' U.S. Plant Pat. No. 21,682 has more purplish-brown leaf blades with less reddish flowers. 'PWHEU0109' U.S. Plant Pat. No. 19,574 has purplish-green leaf blades with less silver in the foliage, broader dark green surrounding the veins and the flowers are creamy-white. 'Mocha Mint' (not patented) has foliage that is purplish-green with less silver, the flower stems are shorter with creamy flowers and the habit is shorter.

*Heuchera* 'Smoke and Mirrors' differs from its parents as well as all other coral bells known to the applicant in the following combined traits:

1. The medium-sized, rounded, leaf blades are shallowly dissected and mostly flat.

2. Leaves are silvery with strong purplish undertones in spring and become silver with deep green surrounding the veins in summer.
3. The upper surface is slightly shiny and the lower surface is strongly-shiny, and both surfaces are finely-puberulent.
4. Produces flowers with deep reddish calyxes beginning early summer on moderately-dense heavily-branched panicles.
5. Produces medium-sized clumps and many individual leaves.
6. Plant is vigorous and not prone to melting out with high temperatures and high humidity.

BRIEF DESCRIPTION OF THE DRAWINGS

The photographs of the new plant demonstrate the overall appearance of *Heuchera* 'Smoke and Mirrors' including the unique traits. The colors are as accurate as reasonably possible with modern color reproductions. Some slight variation of color may occur as a result of lighting quality, intensity, wavelength, and direction or reflection.

DETAILED BOTANICAL DESCRIPTION

Figure 1:
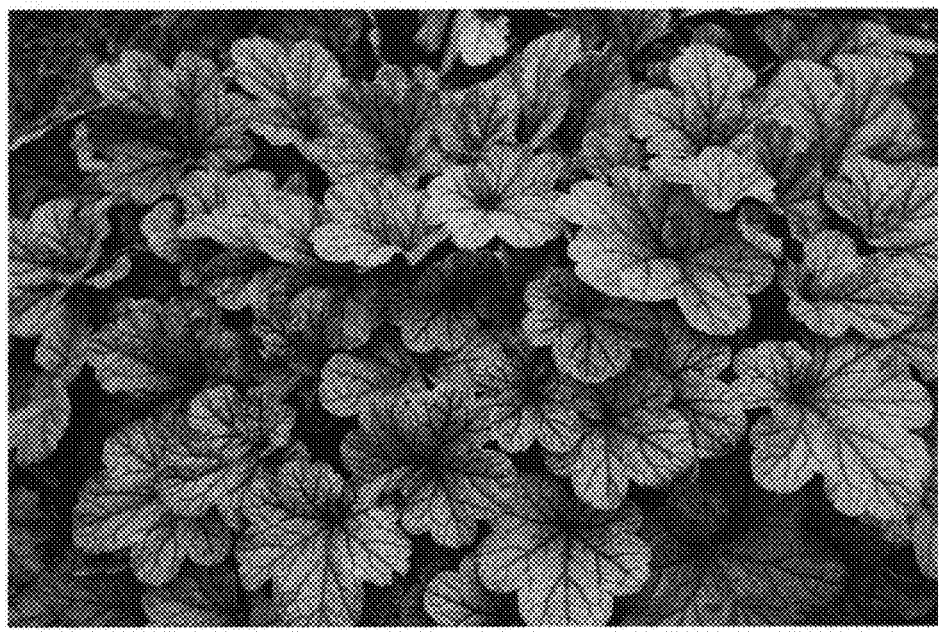
FIG. 1 shows a two-year-old plant just before flowering with intense silver.
Figure 2:
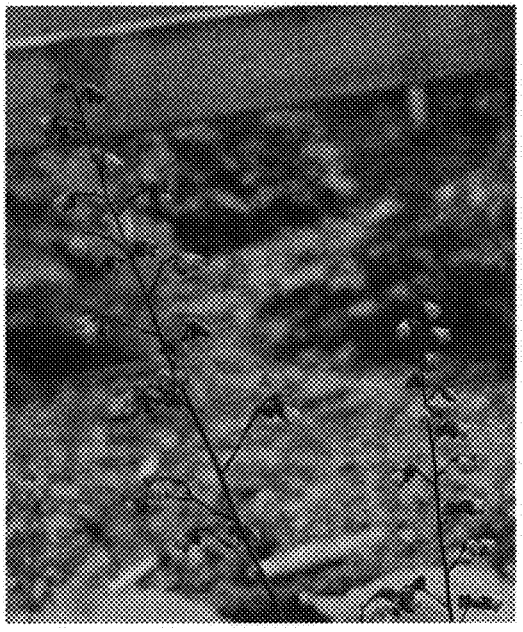
FIG. 2 shows a close-up of the flower scapes.

The following description is based on a two-year-old plant growing in a lightly shaded greenhouse in Zeeland, Mich., USA. The new plant has not been grown under all possible environments and may phenotypically appear different under different conditions such as light, temperatures, fertilizer, and water, without any difference in genotype. The color descriptions used are from the 2015 edition of The Royal Horticultural Society Colour Chart except where common dictionary terms are used.

Parentage: Female or seed parent was the proprietary plant 12-242-08 comprising *Heuchera* 'Mocha' U.S. Plant Pat. No. 18,386, 'PWHEU0109' U.S. Plant Pat. No. 19,574 and 'Stainless Steel' U.S. Plant Pat. No. 23,349 and the male or pollen parent was K11-52-15 comprising 'Milan' U.S. Plant Pat. No. 21,682 and 'Mocha Mint' (not patented);

Plant habit: Hardy herbaceous perennial with basal rosette of foliage; mounded foliage about 22 cm tall and 48 cm in diameter with scapes to about 78 cm tall; stems to about 6.5 cm long and 10.0 mm diameter at base completely covered with petiole stipules, with about 30 leaves per stem and 3 main stems per plant;

Roots: Fibrous, finely branched; nearest RHS NN155B depending on soil type;

Growth rate: Vigorous, rapid; rooting from cutting in two weeks and finishing in three-liter container in about 3 months;

Foliage: Rounded; shallowly penta-lobed (dissected about 5 mm); mostly flat; apex and lobe apices micro-apiculate; base cordate, margin crenate and ciliolate; adaxial surface micro-puberulent, abaxial micro-puberulent; glossiness moderate adaxial and strong abaxial;

Leaf blade size: To about 13.0 cm wide and 13.5 cm long, average about 11.0 cm wide and 11.5 cm long;

Leaf color: Spring and young emerging leaves adaxial nearest RHS N186D near petiole and transitioning to a blend of RHS N187B and RHS N186D narrow area surrounding veins RHS 187A, spring young emerging leaves abaxial blend of nearest RHS 187B and RHS N186D; mature mid-season leaves adaxial blend nearest RHS 189D and RHS 198B with area surrounding veins nearest RHS N189A; midseason abaxial nearest RHS N186D; overwintered adaxial blend between RHS 191C and RHS 198C with thin area surrounding veins nearest blend between RHS NN137A and RHS 139A, abaxial overwintered nearest N186C;

Leaf quantity: Dense, about 30 per division and 90 per plant;

Veins: Palmate, hirsutulous abaxial and puberulent adaxial; costate abaxial and nearly flat adaxial;

Vein color: On emerging or early spring foliage adaxial blend nearest RHS 182B and RHS N187B, emerging or early spring abaxial nearest RHS 182B; mid-season flowering time adaxial nearest blend of RHS 176B and RHS 182B; mid-season and flowering time abaxial main veins nearest RHS 1482B and secondary veins nearest RHS N186C; overwintered veins adaxial nearest RHS 146C near petiole and distally RHS 147B, abaxial overwintered veins nearest RHS 182B and secondary veins nearest RHS N186C;

Petiole: Terete, base amplexicaul; straight, stiff; outwardly to drooping with outer leaves and slightly upright with inner leaves; with pubescent hairs to about 3.0 mm long; to about 14.0 cm long and 3.5 mm across at base above stipule, average about 12.0 cm long and about 3.0 mm across above stipule;

Petiole color: Emerging leaf nearest blend between RHS 182B and RHS 183B; mature leaf nearest blend between RHS 183B and RHS 147B; overwintered leaves variable with some regions nearest RHS 146B and others blushed heavily to lightly with RHS N186C;

Stipule: At base of petiole; puberulent abaxial and glabrous adaxial; about 12.0 mm long and about 8.0 cm wide at base with two distally-flared acute appendages about 2.0 mm long;

Stipule color: Adaxial between RHS 64B and RHS 64A with two longitudinal stripes about 1.0 mm wide running along margins of nearest RHS 195B; abaxial nearest RHS N148B with moderate blush of RHS 187B and two longitudinal margin stripes nearest RHS 195B;

Peduncle: Panicle; terete; stiff; pubescent; mostly upright; to about 78.0 cm long and 4.0 mm diameter at base, average about 67.0 cm tall and about 3.5 mm diameter; about five per plant with up to 400 flowers per panicle, average about 300; heavily compound-branched panicle with up to 20 branches per peduncle up to about 8.0 cm long and about 1.0 mm diameter at base, decreasing in size distally, average 20 branches per panicle; branches outwardly at about 45 degree angle to main peduncle; flower density moderate;

Flowering longevity: Panicle effective for about five weeks;

Flower density: Moderately dense;

Peduncle color: Lighter than RHS 146D, blushed with nearest RHS 183B;

Pedicel: Terete, finely puberulent, average about 2.5 mm long and 0.5 mm diameter; Pedicel color: nearest RHS 178B;

Buds one day prior to opening: Oblong ellipsoidal; rounded apex and attenuate base; puberulent; about 5.0 mm long and 2.0 mm diameter;

Bud color one day prior to opening: Proximal portion nearest blend of RHS 176D and RHS 180D, becoming nearest RHS 176C toward center and nearest RHS 60C toward apex;

Flower: Perfect, campanulate, actinomorphic, about 9.0 mm long to exserted style and 5.0 mm in diameter at face; corolla to 8.0 mm long and 5.0 mm diameter; individual flowers lasting about 4 days on plant or as cut flower; rarely persistent;

Flower attitude: Upwardly to outwardly;

Calyx: Five sepals; apex acute; about 8.0 mm long and 5.0 mm wide, base fused in proximal 4.5 mm to form hypanthium; puberulent abaxial, glabrous adaxial; rarely persistent;

Calyx color: Abaxial base nearest blend of RHS 176D, RHS 195A and RHS 180D and distally nearest RHS 59B at apex; adaxial apex nearest RHS 59B, center nearest N155C; proximally nearest RHS 167D at base;

Petals: Five, oblanceolate to spatulate, acute apex and attenuate base; margin entire, glabrous abaxial and adaxial; adnate to inner sepals in proximal 0.5 mm; about 3.0 mm long and 1.2 mm wide at middle;

Petal color: Abaxial and adaxial nearest RHS 70A;

Androecium: Five adnate to adaxial calyx about 1.0 mm above base;

*Filaments*.—Five, thin, glabrous; about 2.0 mm long and less than 0.3 mm diameter; color nearest RHS 59C.

*Anthers*.—Ellipsoidal, distinct, basifixed, longitudinal; color nearest RHS N187A.

*Pollen*.—Abundant; color nearest RHS 8D.

Gynoecium: One, two-beaked; half-inferior; bifid style with pistil split at ovary; 9.0 mm long;

*Style*.—Bifid; exserted; split apart at apex of ovary; about 4.5 mm long and about 0.5 mm diameter; color between RHS 59C and RHS 59D.

*Stigma*.—Acute apex, about 0.1 mm diameter; color darker than RHS 59A.

*Ovary*.—Half-inferior, about 4.5 mm long and 3.0 mm diameter; ellipsoidal to globose; apex acute, base rounded; color nearest RHS 145C.

Fruit: Two-beaked ellipsoidal capsule; about 4.5 mm long and 3.0 mm across; color nearest RHS 200B;

Seed: Thin ellipsoidal; less than 1.0 mm long and less than 0.5 mm wide; color between RHS 202A and RHS 200A;

Disease and pest tolerance: The new plant grows best with ample moisture and drainage in either sun or shade. Cold hardy from USDA zones 4 to 9. Other resistance and tolerance outside of that normal for *Heuchera* is not known.

It is claimed:

1. A new and distinct *Heuchera* plant named 'Smoke and Mirrors' as herein described and illustrated.

* * * * *